Aug. 13, 1974

G. MERRILL

Plant Pat. 3,589

PEACH PLANT

Filed Oct. 3, 1972

United States Patent Office

Plant Pat. 3,589

Patented Aug. 13, 1974

3,589

PEACH PLANT

Grant Merrill, 416 N. Anderson Road,
Exeter, Calif. 93221

Filed Oct. 3, 1972, Ser. No. 294,669
Int. Cl. A01h 5/03
U.S. Cl. Plt.—43 1 Claim The present invention relates to a peach tree and more particularly to a new and distinct variety thereof broadly characterized by a tree of medium to large size bearing regularly and heavily for its season relatively large fruit with from half to nearly all of its skin surface colored bright red with a bright yellow under color, with scant pubescence, and with freestone yellow flesh that holds its firmness when ripe so long on the tree that the first picking is still firm when the last fruit is ready to pick, so that the fruit may be harvested in one picking, or if the tree is properly pruned, may be mechanically harvested in one picking without excessive damage to the fruit.

The instant variety most nearly resembles June Lady (U.S. Plant Pat. No. 3,022) and Harmony (U.S. Plant Pat. No. 2,152) which have the same parents, or breeding, as the instant variety, but is an improvement on June Lady in ripening about a week to ten days later and in being freer from the stone, and is an improvement on Harmony in having more red skin color and in remaining firm longer on the tree without softening thus allowing a tree to be harvested in one picking.

I originated the present variety near Red Bluff Tehama County, Calif., by cross pollinating, without bagging protection, Fortyniner (unpatented) with Gemfree (U.S. Plant Pat. No. 1,409). One of the resulting seedlings was then grafted onto a tree near Exeter, Tulare County, Calif., where its characteristics proved identical to those of the original tree, and worthy of commercial use.

The accompanying drawing is an oil painting of a characteristic mature fruit of the subject variety showing the shape and skin color.

Referring now more specifically to the pomological characteristics of this new and distinct variety of peach tree, the following is an outline description thereof observed under the ecological conditions prevailing in Tulare County, Calif. All major color plate identifications are by reference to Maerz and Paul's Dictionary of Color, First Edition.

TREE

Generally: Medium to large size, vigorous, vase shaped as usually pruned.
Productivity: Heavy bearer for its season, sets moderately to heavily.
Trunk: Straight, medium stocky, shaggy, gray when mature.
Main branches: Straight except where bent by heavy cropping, gray on older branches, brown on younger branches.
Lenticels: Medium in quantity, medium in size.
Twigs: Medium size, medium internode length, green on current growth, reddish brown on older growth.

LEAVES

Source: From center stock of new growth 18 to 24 inches in length.
Size: Generally medium to large, 6 to 8 inches in length, 1 to 1¾ inches wide, medium thickness.
Shape: Lanceolate, tip acuminate.
Color: Upper surface dark green, lower surface lighter green; veins, very light yellowish green.
Class: Classes 2 and 3 (Meador and Blake: Proceedings of the American Society for Horticultural Science, Vol. 37, p. 203).
Margin: Crenate.
Glands: Reniform, located on petiole and base of leaf.
Stipules: On base of leaf, dropping off early.

FLOWERS

Buds: Medium to small in size, pubescent, plump, free.
Season: Medium early, about with Elberta.
Blossoms: Medium small in size, pink to pinkish-salmon, abundant pollen.

FRUIT

Maturity: First picking June 25, 1971, last picking June 30, 1971—a late season.
Form: Variable, generally globose to cordate, with some tip.
Size: 2⅜ inches axially, 2½ to 3 inches transverse in suture plane, 2½ to 2⅞ inches at right angle to suture plane.
Suture: Inconspicous to shallow, extends from base beyond but discontinuous at apex, has slight depression beyond pistil point.
Dorsal surface: Rounded.
Cavity: Abrupt, elongated in suture plane, depth ¼ to ½ inch, breadth ½ to ¾ inch, markings same as skin hereinafter described.
Base: Retuse.
Apex: Mucronate.
Pistil point: Short.
Stem: About ⅛ to 3/16 inch in length, about ⅛ inch in diameter.
Skin: Medium thick, tenacious to flesh when firm ripe, separates when soft ripe; scant, short pubescence; color, light yellow undercolor 9L3 with red blush blaze red 3J11 to medium red 5K11.
Flesh: Complete freestone; moderate amygdalin; moderate juice; moderate, fine fibers; mild, delicate, distinct aroma; texture firm for one to two weeks on the tree when ready to pick, ripens evenly throughout.

STONE

Tenacity: Completely free.
Fibers: Short, few.
Size: Medium. 1¼ to 1¾ inches long, ⅞–1⅛ inches wide, ¾ to ⅞ inches thick.
Form: Obovate; oval hilum, acuminate apex, equal and unequal sides; base, some straight, some oblique.
Surface: Irregularly furrowed near base and near apex; pitted toward base; pits, some round, some oval.
Ventral edge: Thick, many small furrows.
Dorsal edge: Generally one small groove, extends from base but interrupted toward tip.
Color: Reddish brown when fresh, tan when dried.
Tendency to split: Little.

USE

Markets: Local and long distance shipment.
Quality: Excellent shipping, good eating.

Although the new variety of peach possesses the desired characteristics under the growing conditions near Exeter, Tulare County, Calif., having first been observed near Red Bluff, Tehama County, Calif., it is to be understood that variations of the usual magnitude in the characteristics incident to the growing conditions, fertilization, pruning, thinning and pest control are to be expected.

Having thus described and illustrated my new variety of peach tree, what is claimed is:

1. A new and distinct variety of peach substantially as illustrated and described, which is characterized by a medium to large tree, bearing regularly and heavily for its season relatively large fruit with skin colored from half to nearly all of its surface with bright red and with a yellow undercolor, with scant pubescence and with freestone yellow flesh that holds its firmness while on the tree after ripening so that the first fruit is still firm when the last fruit is ready to pick, allowing the fruit to be harvested in one picking, or if the tree is properly pruned it may be mechanically harvested in one picking without excessive damage to the fruit; and which most nearly resembles June Lady (Plant Pat. 3,022) and Harmony (Plant Pat. 2,152), but is an improvement thereon in that it ripens its fruit about a week later than June Lady and is freer from the stone, and is an improvement on Harmony in having more red color on its skin and in remaining on the tree when ripe without softenig so that it may be harvested in one picking.

No references cited.

ROBERT E. BAGWILL, Primary Examiner